(12) United States Patent
Dalmases Barjoan et al.

(10) Patent No.: US 7,964,749 B2
(45) Date of Patent: Jun. 21, 2011

(54) PROCESS FOR OBTAINING VALINE DERIVATIVES USEFUL FOR OBTAINING A PHARMACEUTICALLY ACTIVE COMPOUND

(75) Inventors: Pere Dalmases Barjoan, Sant Feliu De Llobregat (ES); Joan Huguet Clotet, Sant Joan Despi (ES)

(73) Assignee: Inke, S.A., Castellbisbal (ES)

( * ) Notice: Subject to any disclaimer, the term of this patent is extended or adjusted under 35 U.S.C. 154(b) by 521 days.

(21) Appl. No.: 12/090,729

(22) PCT Filed: Oct. 19, 2006

(86) PCT No.: PCT/EP2006/067569
§ 371 (c)(1),
(2), (4) Date: Apr. 18, 2008

(87) PCT Pub. No.: WO2007/045675
PCT Pub. Date: Apr. 26, 2007

(65) Prior Publication Data
US 2010/0240919 A1 Sep. 23, 2010

(30) Foreign Application Priority Data
Oct. 20, 2005 (ES) .................................. 200502558

(51) Int. Cl.
*C07C 233/31* (2006.01)
*C07C 305/24* (2006.01)
(52) U.S. Cl. ............... 558/53; 558/54; 558/56; 562/567
(58) Field of Classification Search .................. None
See application file for complete search history.

(56) References Cited

U.S. PATENT DOCUMENTS

| 7,439,261 B2 * | 10/2008 | Verardo et al. ................ 514/381 |
| 7,728,021 B2 * | 6/2010 | Dalmases Barjoan et al. .............................. 514/381 |
| 2009/0124577 A1 * | 5/2009 | Rafecas Jane et al. ......... 514/64 |

FOREIGN PATENT DOCUMENTS
WO  WO 2004/026847  *  4/2004

* cited by examiner

*Primary Examiner* — Fiona T Powers
(74) *Attorney, Agent, or Firm* — Cozen O'Connor

(57) ABSTRACT

The invention provides a method for obtaining the intermediate (II), useful for manufacturing Valsartan and a drug directed to a treatment of arterial hypertension or heart failure. The process comprises a) Imination of the aldehyde group of a compound (VII) by L-Valine (IV) salts with organic or inorganic bases and a polar solvent or water, where X means halogen or an —OSO2R group, where R is CF3, tolyl, methyl or F; to give an imine-type compound (VIII), where B+ is the protonated form of an organic base or an alkaline cation; b) Reduction of the imine group of the compound (VIII) followed by acidification, to give the compound (VI); and c) N-Acylation of the compound (VI) with valeryl chloride to give the compound (II). Steps a) and b) can be performed in a "one pot" reaction.

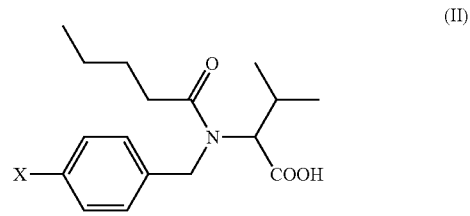

(II)

20 Claims, No Drawings

PROCESS FOR OBTAINING VALINE DERIVATIVES USEFUL FOR OBTAINING A PHARMACEUTICALLY ACTIVE COMPOUND

FIELD OF THE INVENTION

The present invention relates to a method for obtaining intermediates useful for obtaining a pharmaceutically active compound for manufacturing a drug for the treatment of arterial hypertension or heart failure.

In particular, the present invention relates to a method for obtaining intermediates useful in the synthesis of Valsartan.

BACKGROUND OF THE INVENTION

Spanish patent ES2084801T (equivalent to European patent EP 443983) describes acyl compounds, one of them is Valsartan of formula (I):

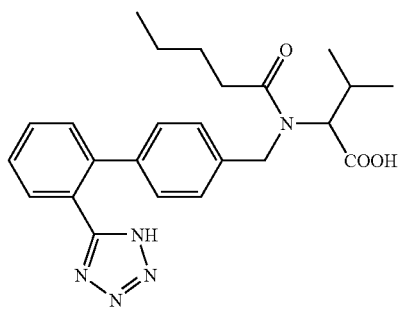

I

Said Spanish patent describes the preparation of Valsartan by converting a phenyl substituent ($Z_1$) into tetrazole, where $Z_1$ is a group convertible into tetrazole. The examples of said patent describe the specific case in which $Z_1$ is a cyano group or a protected tetrazole ring. This is followed by final deprotection of the carboxylic acid group, where R is preferably methyl or benzyl and, if this is the case, of the tetrazole ring protecting group, preferably a trityl group.

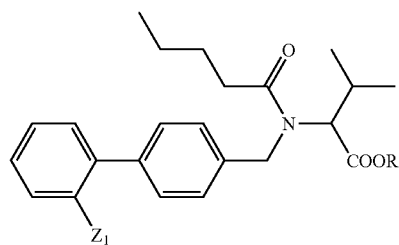

This patent leaves aspects to be improved, such as the use of azide in the last synthesis steps, with the attendant risk of explosions if sodium azide is used, or environmental problems if tributyl tin azide is used.

Another negative aspect lies in the use of bulky protective groups both for the tetrazole ring (trityl group) and the carboxylic acid of the valine moiety (benzyl group), which very considerably increase the molecular weight of the last synthesis intermediate. This molecular weight is drastically reduced in the final hydrolysis to give Valsartan, thus resulting in a process of low atomic efficiency. This further creates a considerable amount of residues and increases the number of synthesis steps in the process.

Patents DE4313747, DE4407488, U.S. Pat. No. 5,596,006, EP594022 and WO9609301 describe the synthesis of sartans by formation of the biphenyl system by reacting an aryl halide with 2-(1H-tetrazol-5-yl)phenylboronic acid in the presence of a palladium catalyst.

European patent application EP1533305 describes a method for obtaining Valsartan by means of reductive amination reaction of a biphenyl aldehyde with protected L-valine with a benzyl group which has to be eliminated. The tetrazole group is formed in the penultimate step of the synthesis.

International patent application WO2004/026847 describes a similar process in which reductive amination of a biphenyl aldehyde takes place, in which the tetrazole group is previously formed and protected, with protected L-Valine in the carboxylic acid function.

There therefore still remains a need for a process for obtaining Valsartan that is safe, ecological and with high yields and few synthesis steps and from simple and commercially available starting products. Additionally, it must be possible to apply the process on an industrial scale and to avoid racemisation and the consequent separation of enantiomers.

Patent application ES200400949, incorporated herein in its entirety as reference, describes a process for the synthesis of Valsartan that includes reaction of the intermediate (II) with a boronic acid of formula (III) in order to give Valsartan (I):

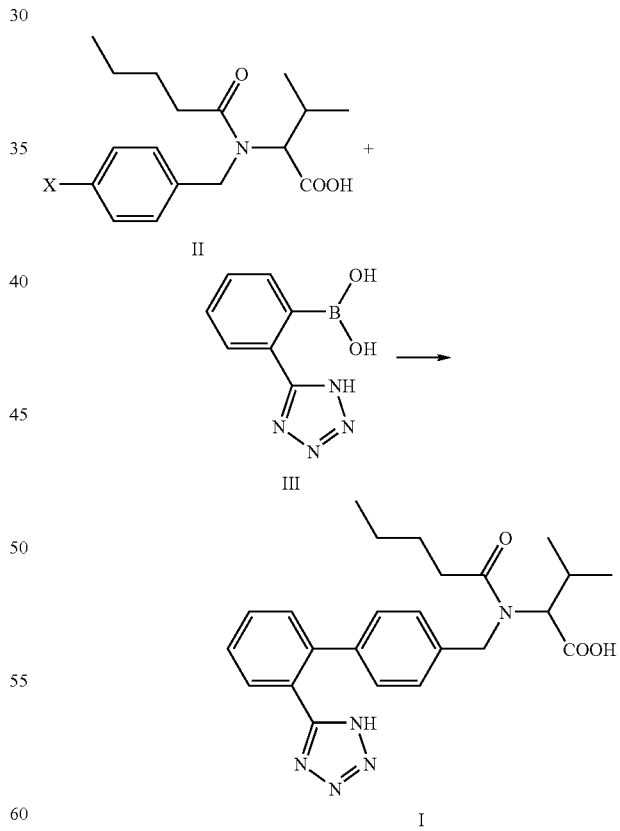

Preparation of the Intermediate (II), in accordance with patent application ES200400949, comprises: a) alkylation of the L-Valine (IV) with a halide of formula (V) to give a compound of formula (VI) followed by b) acylation with valeryl chloride.

Scheme I

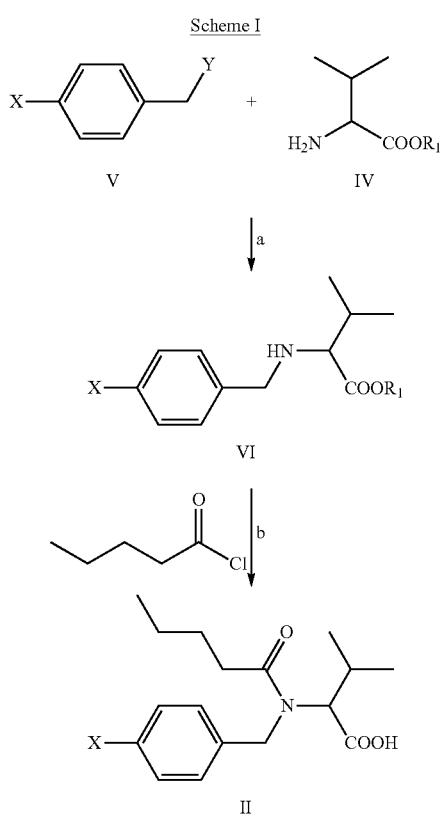

In the alkylation step the carboxylic acid must be protected in the form of silyl ester to prevent the formation of the benzyl ester. Furthermore, the dialkylation compound in the nitrogen of the L-Valine is inevitably formed in variable proportions and is difficult to eliminate.

In the acylation step of intermediate (VI), moreover, the reaction conditions are critical, and a restricted range of reaction parameters has to be used in order to prevent partial racemisation of compound (II) that would involve additional purifications.

This process presents disadvantages that hinder its application on an industrial scale and that are susceptible of improvement in order to reduce costs, generate less waste and improve the yield of the synthesis, as well as allow the utilisation of more easily handled reagents.

DESCRIPTION OF THE INVENTION

A first aspect of the present invention is to provide an industrially viable process for obtaining the synthesis intermediate (II), useful in the preparation of Valsartan, and permitting it to be obtained with high yields and without racemisation.

A second aspect of the invention is to provide a method for obtaining the synthesis intermediate (II) with few synthesis steps.

DEFINITIONS

The term "work up" is taken to mean the work of isolation and/or purification that is carried out once the reaction has finished. This involves, for example, extractions or precipitations in an aqueous medium.

The term "one pot" is taken to mean a series of consecutive reactions that are carried out without isolating the respective intermediates.

DETAILED DESCRIPTION OF THE INVENTION

The object of the present invention is to provide a new process for obtaining the intermediate of formula (II), that permits it to be obtained with good yields, without racemisation, free from impurities and without problematic safety and environmental aspects.

Advantageously, with the process according to the first and second aspects of the invention the intermediate of formula (II) is provided free from impurities, unlike the processes described in the state of the art prior to this application.

The process for obtaining the intermediate of formula (II), useful for the synthesis of Valsartan,

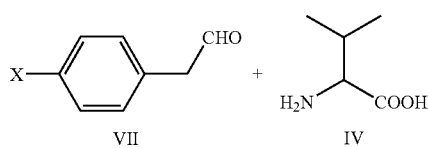

in accordance with the first aspect of the invention, is characterised in that it comprises the following steps:

a) Imination of the aldehyde group of a compound of formula (VII) by salts of the L-Valine (IV) with organic or inorganic bases and a polar solvent or water:

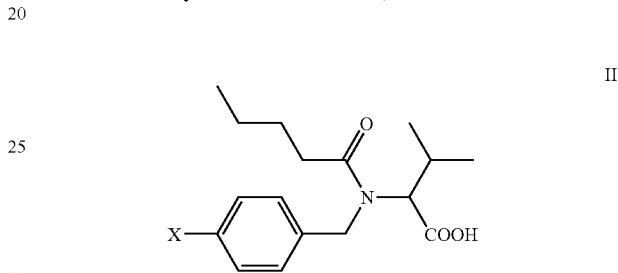

where:

X means halogen or an —$OSO_2R$ group, where R is $CF_3$, tolyl, methyl or F;

to give a compound of imine type or Schiff base of formula (VIII):

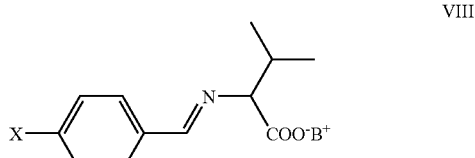

where:

X has the meaning defined above and $B^+$ is the protonated form of an organic base or an alkaline cation.

b) Reduction of the imine group of the compound of formula (VIII) followed by acidification, to give the compound of formula (VI):

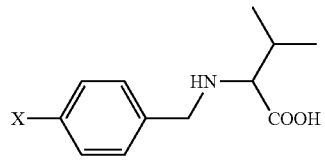

c) N-Acylation of the compound of formula (VI) with valeryl chloride to give the compound of formula (II):

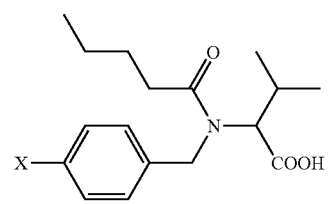

Advantageously, the process according to the invention does not use protective groups of the carboxylic acid group of the valine moiety in preparation of the synthesis intermediate (VI). This is advantageous for what is understood as the atomic efficiency of the process, i.e. the proportion of atoms of the respective starting reagents that are incorporated into the desired product is optimum, and this translates into a considerable reduction of the amount of residues to be treated.

Schema II below shows the complete sequence of steps:

Scheme II

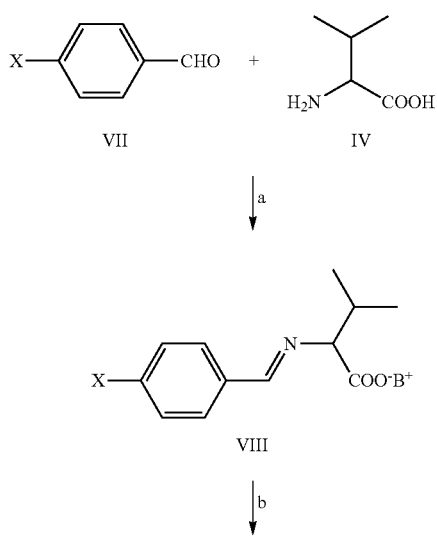

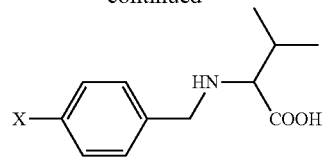

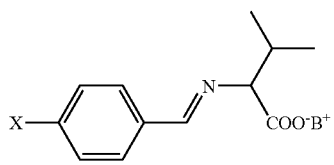

In accordance with step a), according to the first aspect of the invention, the intermediate of formula (VIII) is obtained:

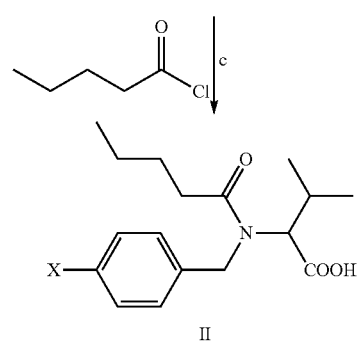

where X means halogen or an —OSO$_2$R group, where R is CF$_3$, tolyl, methyl or F, and B$^+$ is the protonated form of an organic base or an alkaline cation, by means of an imination reaction of a benzaldehyde substituted in the position for (VII) by salts of the L-Valine with organic or inorganic bases.

The L-Valine is mixed with the 4-substituted benzaldehyde (VII) in the presence of an organic or inorganic base in equimolar proportion in relation to the L-Valine and a polar solvent or water at a temperature between 0° C. and the boiling temperature of the solvent, preferably between 10° C. and 35° C.

A substituted amine-type organic base may be used, such as triethylamine, trialkylamine, diisopropylethylamine (DIPEA) or a metallic alcoxide or hydroxide to form a salt of the L-Valine with an alkaline metal.

The salt of an alkaline metal of the L-Valine can be prepared in situ in the reaction medium by the addition of bases such as hydroxides and alcoxylates, for example sodium hydroxide, potassium hydroxide, sodium methylate or sodium ethylate in a solution in methanol and optionally water. The sodium salt can also be prepared independently by addition of a metal in elemental state, such as metallic sodium, to a solution of L-Valine in a polar solvent in the absence of water, such as anhydrous methanol.

The solvent of the reaction can be selected between water or a protic polar solvent. Preferably, the protic polar solvent is an alcohol, such as methanol, ethanol, 2-propanol, but more preferably methanol.

Alternatively, in order to encourage formation of the imine compound of formula (VIII), methods can be used to remove the water from the medium, such as by using molecular sieves or azeotropic distillation, in which case a polar solvent will be used during the reaction for obtaining (VIII).

It is possible to isolate the imine or Schiff base (VIII) by evaporating the solvent.

Below, in accordance with step b) according to the first aspect of the invention, the intermediate (VIII) is submitted to reductive conditions to obtain the compound (VI).

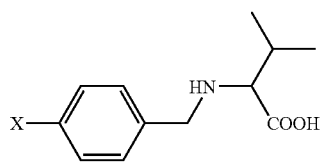

VI

Preferably, the reaction takes place in an alcoholic medium using borohydride as reducing agent, such as sodium borohydride, lithium borohydride, calcium borohydride, sodium cyanoborohydride or sodium triacetoxyborohydride.

As an alternative, the reduction can also be carried out by means of catalytic hydrogenation in the presence of hydrogen and of a metallic catalyst at atmospheric pressure, or by transfer of hydrogen in the presence of a metallic catalyst and a hydrogen donor such as formic acid, 2-propanol, ethanol, etc. The metallic catalyst used can be Raney-Nickel or a palladium, rhodium or ruthenium catalyst, preferably a palladium catalyst.

Preferably, the reduction is carried out with sodium borohydride. Under these imine bond reduction conditions, surprisingly, racemisation of the chiral centre present in the molecule is prevented. This is an additional advantage over methods that involve the utilisation of carboxylic group protective groups, since the deprotection conditions can lead to racemisation.

This process has the advantage that it does not require protection of the carboxyl group of the L-Valine. The reductive amination reaction has the additional advantage of preventing formation of the dialkylation product.

Next, and in accordance with step c), the compound (VI) obtained is made to react with valeryl chloride in order to provide the intermediate (II):

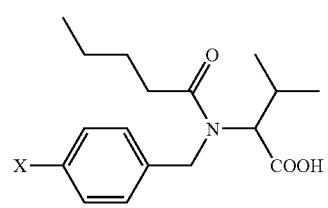

II where X means halogen or an —OSO$_2$R group, where R is CF$_3$, tolyl, methyl or F.

This step c) of the process is characterised in that it consists in N-acylation of the compound of formula (VI) with valeryl chloride, without the protection of carboxylic acid:

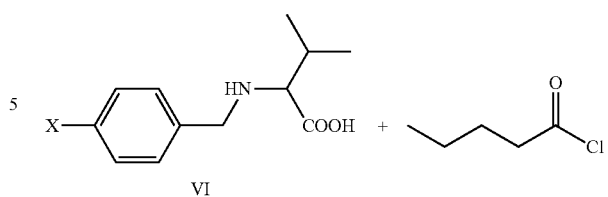

VI in the presence of an aprotic organic solvent and an organic or inorganic base and at a temperature between −20 and 40° C., to give the compound of formula (II):

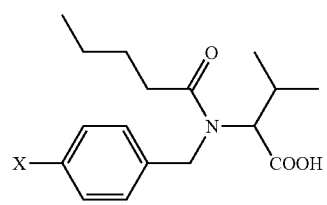

II

Preferably, said aprotic organic solvent is selected from tetrahydrofuran (THF), dimethoxyethane (DME) and acetonitrile. More preferably still, it is tetrahydrofuran (THF).

Preferably, an organic base will be selected from a heterocyclic compound that contains one or more atoms of nitrogen. Preferably, said heterocyclic compound with at least one atom of nitrogen is chosen from pyridine or pyridines substituted with one or more methyl groups, such as collidines or lutidines; or imidazole or imidazole substituted with a methyl group such as 2-methylimidazole or 4-methylimidazole. More preferably still, 2-methylimidazole is used.

The reaction of step c) takes place in the presence of 1 or 2 equivalents of water in relation to the amount of starting product (VI). Advantageously, the presence of water in said reaction prevents racemisation of the asymmetric carbon.

Advantageously, said N-acylation is carried out at a temperature between −10 and 10° C.

In accordance with the second aspect of the invention, a method is provided for obtaining the synthesis intermediate (II) with few synthesis steps, where the compound of formula (VI) can be obtained by means of a one-pot reaction from the starting products (VII) and (IV), without need to isolate the imine compound (VIII).

With the process according to the second aspect of the invention the compound of formula (II) is achieved with good yields and in two reaction steps, since the one-pot reaction is carried out according to the conditions set out in steps a) and b) to obtain the compound of formula (VI) from simple and commercially available raw materials.

Finally, the product obtained according to the first or second aspects of the invention can be purified by conventional methods such as recrystallisation in a single solvent or in a mixture of a solvent and antisolvent, for example ethanol/water, ethyl acetate/hexane, dichloromethane/heptane, isopropyl acetate/methylcyclohexane.

Surprisingly and unexpectedly, according to the first and second aspects the invention provides a method for obtaining the intermediate of formula (II) without racemisation from a compound of formula (VI) that does not require the protection of the carboxylic acid.

Advantageously, the compound of formula (VI) is obtained with an optical purity of 99.5-100%.

The process described according to the first and the second aspects of the invention permits very good qualities of Valsartan to be obtained and, therefore, the process of subsequent purification of said active ingredient is greatly simplified.

The process of formula (I) for obtaining Valsartan, by means of coupling of the intermediate of formula (VI), referenced in the present invention as intermediate of formula (II), with the boronic acid of formula (VII), is the object of the patent application ES200400949:

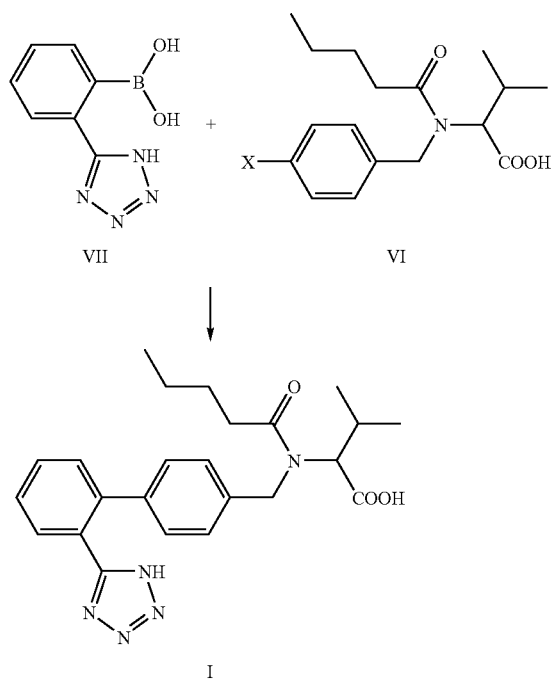

In said application Valsartan is obtained with good chemical yield and high optical purity by means of a process applicable on an industrial scale and starting from simple and commercially available products through synthesis intermediates that do not require protection of the tetrazolic ring or of the carboxylic acid of the L-Valine moiety, nor the use of sodium azide or tributyl tin azide, thereby improving the safety of the process and reducing its environmental impact.

There follow some examples which, by way of non-restrictive example, show some preferred embodiments of the various aspects thereof.

EXAMPLES

Example 1

N-(4-bromobenzyl)-L-Valine

To a mixture formed by 11.7 g (100 mmol) of L-Valine, 100 mL of methanol and 21 mL (110 mmol) of a 30% methanolic solution of sodium methoxide is added 16.7 g (90 mmol) of 4-bromobenzaldhehyde, and this is stirred for 1 h. The mixture is cooled to −10° C. and 1.9 g (50 mmol) of NaBH$_4$ is added in portions, keeping the temperature below 0° C. After 90 minutes of reaction time, 100 mL of H$_2$O are added slowly followed by 20 mL of toluene and the pH is adjusted to 5 with HCl 3N. The solid obtained is filtered and washed with H$_2$O to give 23.7 g (92%) of N-(4-bromobenzyl)-L-Valine.

Min. DSC=256.6° C.
[α]=17.6°
The enantiomeric purity is determined by chiral HPLC giving e.e=100%
IR (KBr, cm-1): 2962, 1606, 1447, 1388, 1208, 1013, 872, 793.
NMR 1H (DMSO, 60° C.), .(ppm): 0.91 (d, 6H, —CH(CH3)2); 1.7-1.9 (m, 1H, —CH(CH3)2); 2.84 (d, 1H, —CHCO2H); 3.7 (dd, 2H, Ar—CH2-); 7.3 (d, 2H, ArH); 7.5 (d, 2H, ArH).

Example 2

N-(4-chlorobenzyl)-L-Valine

In a manner similar to Example 1 and starting out from 11.7 g (100 mmol) of L-Valine, 21 mL (110 mmol) of 30% methanolic solution of sodium methoxide, 12.7 g (90 mmol) of 4-chlorobenzaldhehyde and 1.9 g (50 mmol) of NaBH$_4$, 17.8 g (82%) of N-(4-chlorobenzyl)-L-Valine is obtained.
Min. DSC=241.8° C.
[α]=20.1°
IR (KBr, cm-1): 2960, 1599, 1485, 1444, 1351, 1287, 1209, 1091, 1017, 834.
NMR 1H (DMSO, 60° C.), .(ppm): 0.91 (d, 6H, —CH(CH3)2); 1.7-1.9 (m, 1H, —CH(CH3)2); 2.84 (d, 1H, —CHCO2H); 3.7 (dd, 2H, Ar—CH2-); 7.4 (s, 4H, ArH).

Example 3

N-(4-idobenzyl)-L-Valine

In a manner similar to Example 1 and starting out from 454 mg (3.87 mmol) of L-Valine, 1 mL (5.39 mmol) of 30% methanolic solution of sodium methoxide, 1 g (4.31 mmol) of 4-iodobenzaldhehyde and 83 mg (2.2 mmol) of NaBH$_4$, 1 g (70%) of N-(4-iodobenzyl)-L-Valine is obtained.
Min. DSC=264.2° C.
[α]=13.3°
IR (KBr, cm-1): 2952, 1610, 1485, 1446, 1348, 1284, 1206, 1006, 824, 789.
NMR 1H (DMSO, 60° C.), .(ppm): 0.93 (d, 6H, —CH(CH3)2); 1.7-1.9 (m, 1H, —CH(CH3)2); 2.81 (d, 1H, —CHCO2H); 3.7 (dd, 2H, Ar—CH2-); 7.2 (d, 2H, ArH); 7.7 (d, 2H, ArH).

Example 4

N-(4-(toluen-4-sulphonyl)-benzyl)-L-Valine

In a manner similar to Example 1 and starting out from 8.5 g (72.5 mmol) of L-Valine, 16 mL (86.3 mmol) of 30% methanolic solution of sodium methoxide, 20 g (72.5 mmol) of 4-tosylbenzaldhehyde and 1.4 g (37 mmol) of NaBH$_4$, 20 g (73%) of N-(4-toluen-4-sulphonyl)-benzyl)-L-Valine is obtained.
Min. DSC=219.5° C.
[α]=12.3°
IR (KBr, cm-1): 2957, 1606, 1443, 1373, 1090, 1017, 867, 746, 698.
NMR 1H (DMSO, 60° C.), .(ppm): 0.91 (d, 6H, —CH(CH3)2); 1.7-1.9 (m, 1H, —CH(CH3)2); 2.5 (s, 3H, H3C—Ar—SO2-); 2.82 (d, 1H, —CHCO2H); 3.7 (dd, 2H, Ar—CH2-); 7.3 (d, 2H, ArH); 7.5 (d, 2H, ArH); 7.0 (d, 2H, O2SArH—CH3); 7.7 (d, 2H, O2SArH—CH3).

Example 5

N-(4-bromobenzyl)-N-valeryl-L-Valine

A mixture formed by 11.4 g (40 mmol) of N-(4-bromobenzyl)-L-Valine and 60 mL of THF is cooled to −5° C., and 2.8 mL (50 mmol) of HAcO, 7.6 mL (64 mmol) of valeryl chloride and a solution of 4.9 g (60 mmol) of 2-methylimidazole in 30 mL of THF and 1.4 mL (80 mmol) of $H_2O$ are added to it. The reaction mixture is stirred for 30 minutes at room temperature, 10 mL of methanol is added to it, it is then stirred for a further 15 minutes and 40 mL of $H_2O$ is added to it. The phases are separated and the organic phase is evaporated to dryness and the solid obtained is recrystallised from a mixture of $EtOH:H_2O$ 1:1.

Min. DSC=134.3° C.
$[\alpha]=-68°$

The enantiomeric purity is determined by chiral HPLC, giving e.e=100%

IR (KBr, cm-1): 2957, 1720, 1591, 1472, 1247, 1012, 786.

NMR 1H(CDCl$_3$), .(ppm): 0.8-1.1 (m, 9H, —CH(CH3)2+ —CH2CH3); 1.2-1.5 (m, 2H, —CH2CH3); 1.5-1.8 (m, 2H, —CH2CH2CH3); 2.4 (t, 2H, —CH2CO—); 2.5-2.7 (m, 1H, —CH(CH3)2); 3.8 (d, 1H, —CHCO2H); 4.6 (dd, 2H, Ar—CH2-); 7.1 (d, 2H, ArH); 7.5 (d, 2H, ArH).

Example 6

N-(4-chlorobenzyl)-N-valeryl-L-Valine

In a manner similar to Example 5 and starting from 15 g (62 mmol) of N-(4-chlorobenzyl)-L-Valine, 12 mL (99 mmol) of valeryl chloride and 7.7 g (93 mmol) of 2-methylimidazole, 15.7 g (77%) of N-(4-chlorobenzyl)-N-valeryl-L-Valine is obtained. The solid is recrystallised from a mixture of $EtOH:H_2O$ 1:1.

Min. DSC=128.1° C.
$[\alpha]=-77.9°$

IR (KBr, cm-1): 2957, 1714, 1588, 1471, 1403, 1246, 1095, 792.

NMR 1H(CDCl3), .(ppm): 0.8-1.1 (m, 9H, —CH(CH3)2+ —CH2CH3); 1.2-1.5 (m, 2H, —CH2CH3); 1.5-1.8 (m, 2H, —CH2CH2CH3); 2.4 (t, 2H, —CH2CO—); 2.5-2.7 (m, 1H, —CH(CH3)2); 3.8 (d, 1H, —CHCO2H); 4.6 (dd, 2H, Ar—CH2-); 7.1 (d, 2H, ArH); 7.3 (d, 2H, ArH).

Example 7

N-(4-iodobenzyl)-N-valeryl-L-Valine

In a manner similar to Example 5 and starting from 800 mg (2.40 mmol) of N-(4-iodobenzyl)-L-Valine, 0.47 mL (3.84 mmol) of valeryl chloride and 296 mg (3.60 mmol) of 2-methylimidazole, 635 mg (64%) of N-(4-iodobenzyl)-N-valeryl-L-Valine is obtained. The solid is recrystallised from a mixture of $EtOH:H_2O$ 1:1.

Min. DSC=129.5° C.
$[\alpha]=-52.9°$

IR (KBr, cm-1): 2957, 1719, 1588, 1469, 1403, 1247, 1173, 1105, 1003, 966, 847, 783.

NMR 1H(CDCl3), .(ppm): 0.8-1.1 (m, 9H, —CH(CH3)2+ —CH2CH3); 1.2-1.5 (m, 2H, —CH2CH3); 1.5-1.8 (m, 2H, —CH2CH2CH3); 2.4 (t, 2H, —CH2CO—); 2.5-2.7 (m, 1H, —CH(CH3)2); 3.8 (d, 1H, —CHCO2H); 4.6 (dd, 2H, Ar—CH2-); 7.0 (d, 2H, ArH); 7.7 (d, 2H, ArH).

Example 8

N-(4-(toluen-4-sulphonyl)-benzyl)-N-valeryl-L-Valine

In a manner similar to Example 5 and starting from 12 g (32 mmol) of N-(4-tosylbenzyl)-L-Valine, 6.2 mL (51 mmol) of valeryl chloride and 3.95 g (48 mmol) of 2-methylimidazole, 11 g (75%) of N-(4-toluen-4-sulphonyl)-benzyl)-N-valeryl-L-Valine is obtained. The solid is recrystallised from a mixture of n-Heptane:EtAcO 10:1.

Min. DSC=98.1° C.
$[\alpha]=-57.1°$

IR (KBr, cm-1): 2957, 1714, 1575, 1469, 1362, 1249, 1173, 1092, 862, 748, 688, 660.

NMR 1H(CDCl3), .(ppm): 0.8-1.1 (m, 9H, —CH(CH3)2+ —CH2CH3); 1.2-1.5 (m, 2H, —CH2CH3); 1.5-1.8 (m, 2H, —CH2CH2CH3); 2.3 (t, 2H, —CH2CO—); 2.4 (s, 3H, SO2ArCH3); 2.6 (m, 1H, —CH(CH3)2); 3.7 (d, 1H, —CHCO2H); 4.6 (dd, 2H, Ar—CH2-); 7.1 (d, 2H, ArH); 7.3 (d, 2H, ArH); 7.0 (d, 2H, O2SArH—CH3); 7.7 (d, 2H, O2SArH—CH3).

The invention claimed is:
1. Process for obtaining the synthesis intermediate of formula (II) useful for the synthesis of Valsartan, which comprises:

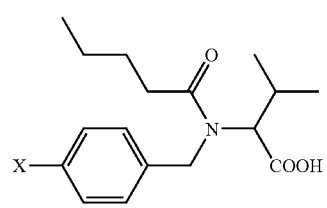

II a) imination of the aldehyde group of a compound of formula (VII) by L-Valine (IV) salts with organic or inorganic bases and a polar solvent or water:

where:

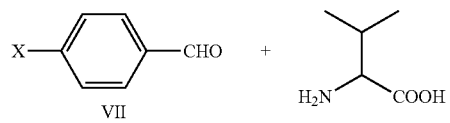

VII

X means halogen or an $OSO_2R$ group, where R is CF3, tolyl, methyl or F;

to give an imine-type compound or Schiff base of formula (VIII):

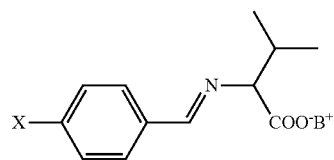

VIII where:
X has the meaning defined above and $B^+$ is the protonated form of an organic base or an alkaline cation;

b) reduction of the imine group of the compound of formula (VIII) followed by acidification, to give the compound of formula (VI):

c) N-acylation, of the compound of formula (VI) with valeryl chloride to

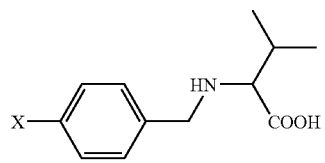

VI give the compound of formula II.

2. Process according to claim 1, wherein said organic or inorganic base is in equimolar proportion in relation to the L-Valine.

3. Process according to claim 1, wherein in said step a) said organic base is chosen from a substituted amine-type compound to form a salt of the L-Valine with an ammonium cation; an alcoxide or metallic hydroxide to form a salt of the L-Valine with an alkaline metal.

4. Process according to claim 1, wherein said step a) of imination is carried out at a temperature between 0° C. and the boiling temperature of the solvent.

5. Process according to claim 4, wherein said temperature is between 10° C. and 35° C.

6. Process according to claim 1, wherein said solvent is chosen from a protic polar solvent.

7. Process according to claim 6, wherein said solvent is an alcohol.

8. Process according to claim 1, wherein in step b) the reduction reaction takes place in an alcoholic medium using a borohydride as reducing agent.

9. Process according to claim 8, wherein said borohydride is chosen from sodium borohydride, lithium borohydride, calcium borohydride, sodium cyanoborohydride or sodium triacetoxyborohydride.

10. Process according to claim 1, wherein in step b) the reduction reaction is carried out by means of catalytic hydrogenation in the presence of hydrogen and of a metallic catalyst at atmospheric pressure or by means of hydrogen transfer in the presence of a metallic catalyst and a hydrogen donor.

11. Process according to claim 10, wherein said metallic catalyst is chosen from Raney-Nickel or a catalyst of palladium, platinum, rhodium or ruthenium, preferably palladium.

12. Process according to claim 10, wherein said hydrogen donor is chosen from formic acid, 2-propanol or ethanol.

13. Process according to claim 1, wherein step c) of N-Acylation takes place in the presence of an aprotic organic solvent and an organic or inorganic base, at a temperature between −20° C. and 40° C. to give the compound of formula (II).

14. Process according to claim 13, wherein it is carried out at a temperature between −10 and 10° C.

15. Process according to claim 13, wherein said aprotic organic solvent is chosen from tetrahydrofuran (THF), dimethoxyethane (DME) and acetonitrile.

16. Process according to claim 15, wherein said solvent is tetrahydrofuran (THF).

17. Process according to claim 13, wherein said organic base is chosen from a heterocyclic compound that contains one or more atoms of nitrogen.

18. Process according to claim 17, wherein said heterocyclic compound with at least one atom of nitrogen is chosen from pyridine or substituted pyridines, collidines or lutidines; or imidazole or imidazole substituted as 2-methylimidazole or 4-methylimidazole.

19. Process according to claim 13, wherein said reaction of N-Acylation takes place in the presence of 1 or 2 equivalents of water in relation to the amount of starting product (VI).

20. Process for obtaining the synthesis intermediate of formula (II), according to claim 1, wherein steps a) and b) are carried out in a one-pot reaction.

* * * * *